US007434372B2

(12) United States Patent
Vanhamel et al.

(10) Patent No.: US 7,434,372 B2

(45) Date of Patent: Oct. 14, 2008

(54) PACKAGING ARTICLE COMPRISING POROUS MATERIAL, AND METHOD OF INTEGRITY TESTING OF SAME

(75) Inventors: Steven Vanhamel, Herk-De-Stad (BE); Thomas Claes, Hasselt (BE)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 11/621,461

(22) Filed: Jan. 9, 2007

(65) Prior Publication Data

US 2007/0107381 A1 May 17, 2007

Related U.S. Application Data

(62) Division of application No. 10/643,026, filed on Aug. 18, 2003, now Pat. No. 7,160,590.

(51) Int. Cl.
*B65B 65/08* (2006.01)

(52) U.S. Cl. ............................ 53/425; 53/428; 53/426; 53/111 R; 422/302; 428/35.7; 428/36.4

(58) Field of Classification Search .................. 53/425, 53/426, 428, 111 R; 422/302; 428/35.7, 428/36.5, 34.3, 35.2
See application file for complete search history.

(56) References Cited

U.S. PATENT DOCUMENTS 3,061,087 A * 10/1962 Scrivens et al. ............. 206/439
3,093,242 A * 6/1963 Huyck et al. ................ 206/210
3,229,813 A * 1/1966 Crowe, Jr. et al. ........... 206/439
3,460,742 A * 8/1969 Langdon ..................... 206/439
3,604,616 A * 9/1971 Greif .......................... 206/439
3,991,881 A * 11/1976 Augurt ....................... 206/439
4,055,672 A 10/1977 Hirsch et al.
4,121,714 A * 10/1978 Daly et al. .................. 206/363
4,461,420 A 7/1984 Horvath
4,539,836 A 9/1985 Hester et al.
5,217,772 A 6/1993 Brown et al.
5,418,022 A 5/1995 Anderson et al.
5,459,978 A 10/1995 Weiss et al.
5,590,778 A * 1/1997 Dutchik ...................... 206/439
5,591,468 A 1/1997 Stockley, III et al.
5,830,547 A * 11/1998 MacKenzie et al. ........ 428/36.1
5,976,299 A 11/1999 Ivey (Continued)

OTHER PUBLICATIONS

Strength and Integrity—The basics of Medical Package Testing by Stephen Franks of TM electronics, Inc., 2001.*

*Primary Examiner*—Thanh K Truong
(74) *Attorney, Agent, or Firm*—Vincent K. Gustafson; Intellectual Property/ Technology Law; David Shofi

(57) ABSTRACT

A packaging article comprises two sheets of material bonded to form a pouch, with one layer comprising a first sheet of a porous material, e.g., Tyvek® film, and a second nonporous sheet overlying and sealed to the first sheet. The second sheet is impermeable to passage of gas therethrough and includes a peelable film, e.g., of polyethylene, in contact with the first sheet of porous material to permit peeling removal of the second sheet from the first sheet. A method of integrity testing includes fabricating a packaging article, pressurizing same with a gas and monitoring pressure to determine package integrity, removing the peelable film, and exposing a packaging article to sterilant gas supplied through the porous first sheet.

35 Claims, 5 Drawing Sheets

U.S. PATENT DOCUMENTS 6,065,597 A 5/2000 Pettersson et al.
6,251,489 B1 6/2001 Weiss et al.
6,460,405 B1 10/2002 Mayer et al.
6,513,366 B1 2/2003 Stauffer
6,609,414 B2 8/2003 Mayer et al.
7,036,287 B1 * 5/2006 Webb .......................... 53/53
7,160,590 B2 1/2007 Vanhamel et al.
2003/0015021 A1 * 1/2003 Mayer et al. ................ 73/40.7

* cited by examiner

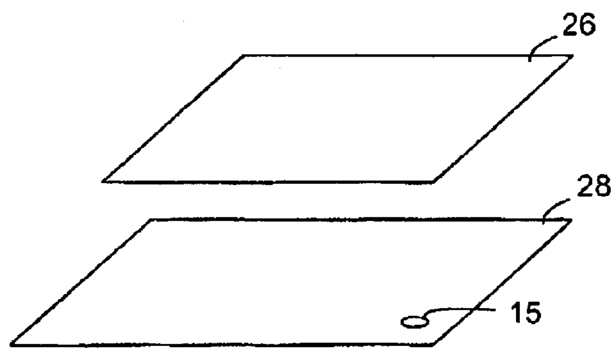
FIG. 3A
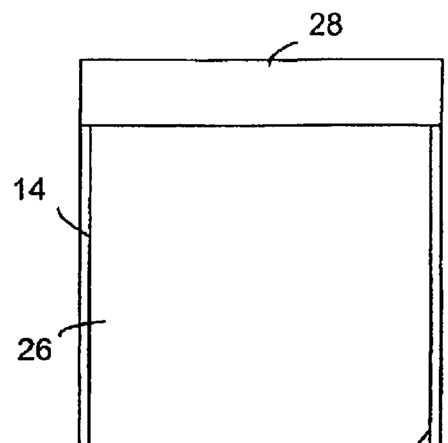
FIG. 3B
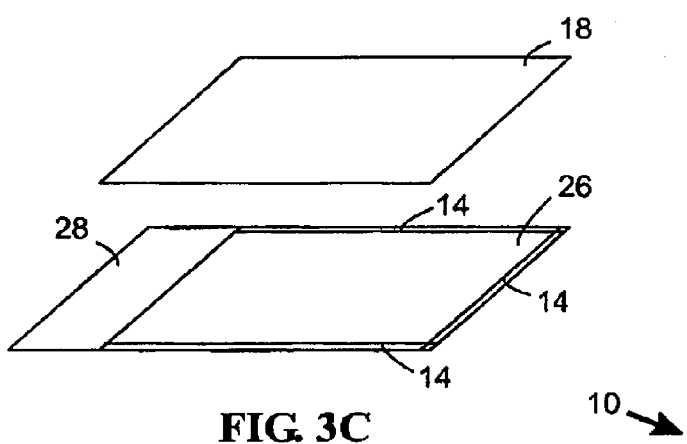
FIG. 3C
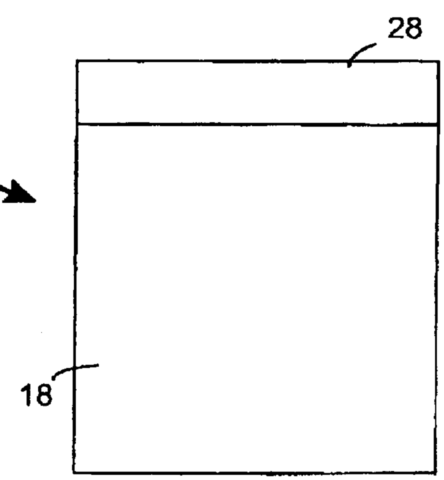
FIG. 3E
10
28
18
FIG. 3D

PACKAGING ARTICLE COMPRISING POROUS MATERIAL, AND METHOD OF INTEGRITY TESTING OF SAME

STATEMENT OF RELATED APPLICATION(S)

This is a divisional application claiming benefit of U.S. patent application Ser. No. 10/643,026, filed Aug. 18, 2003, now issued as U.S. Pat. No. 7,160,590.

FIELD OF THE INVENTION

The present invention relates to composite webs, packaging including such composite webs, and integrity testing of packaging that includes a porous web structural component.

DESCRIPTION OF THE RELATED ART

Many products are packaged in composite packaging that must accommodate sterilization procedures to render the packaged product suitable for its ultimate use. Examples of such products include medical devices that contact the body or body fluids in ultimate use, pharmaceutical therapeutic agents that are packaged for subsequent dispensing, and food and chemicals that are susceptible to degradation and deterioration if contaminated by microbiological agents.

A variety of sterilization procedures have come into use for rendering such packaged products free of deleterious contaminants. Among these sterilization procedures, sterilization by exposure of the package to steam and/or ethylene oxide (ETO) is often employed as a reliable and safe methodology for sterilization of bags and similar containment structures that include gas-porous and non-porous portions. For example, steam- and/or ETO-sterilizable bags commonly have one side that is porous for the sterilant gas and provides a microbiological barrier to maintain the sterilization of the packaged contents after exposure to the sterilant gas, and a second side that is non-porous to the sterilant gas. The porous side of such containers is typically paper or a flash-spun and bonded polymer film, such as Tyvek® film (commercially available from E.I. DuPont de Nemours & Co., Wilmington, Del.). Tyvek® film is formed from high density polyethylene fibers that are flash spun and then laid as a web on a moving bed for consolidation by heat and pressure to form the product sheet-form material, and is a preferred form of porous packaging material for many applications due to its penetration resistance to bacteria, tear strength and puncture-resistant character.

The porous films of such packaging, however, whether paper or synthetic resin-based, have the associated deficiency that they do not permit non-destructive testing of their integrity. In many applications, such as the use of isolator bags that maintain physical separation of product components, purchasers typically desire each bag to be individually tested for seal integrity.

When Tyvek® film is used for fabricating such bags, seal integrity can only be carried out by leak testing using a calorimetric fluid such as methylene blue liquid, which however renders the bag unsuitable for subsequent use. In other packaging material applications, bags are typically subjected to non-destructive pressure testing, in which the bag is filled with compressed air, and pressure loss as a function of time is then monitored to verify fluid-tightness of the bag and integrity of its seams and surfaces. Due to the presence of the porous sheet material in the bag, however, this mode of testing cannot be used.

Accordingly, there is a continuing and critical need in the art for improved structures in steam- and/or ETO-sterilizable bags and other containment structures including porous fibrous web sheets, which require integrity testing for qualification for subsequent use.

SUMMARY OF THE INVENTION

The present invention relates to porous web composites, packaging comprising same, and integrity testing of packaging that includes a porous web structural component.

In one aspect, the invention relates a method of integrity testing a packaging article by pressure retention testing and rendering said packaging article permeable to sterilant gas for sterile packaging of a product article therein after said pressure retention testing, and sterilizing the packaging, said method comprising:

- (a) fabricating said packaging article with a sheet form structural component including: a first sheet of a porous material that is permeable to passage of sterilant gas therethrough in exposure to a sterilant gas environment; and a second sheet overlying and sealed to the first sheet, wherein said second sheet (i) is non-porous to passage of said sterilant gas therethrough and (ii) comprises a peelable film in facial contact with the first sheet of porous material, said peelable film permitting peeling removal of the second sheet from the first sheet to expose the first sheet for passage of said sterilant gas therethrough;
- (b) pressurizing said packaging article by a compressed gas and monitoring pressure retention by the packaging article to determine its integrity;
- (c) after completion of step (b) with a verification of said integrity, peelingly removing the second sheet from the first sheet to expose the first sheet for passage of said sterilant gas therethrough; and
- (d) after step (c), exposing said packaging article to said sterilant gas to sterilize said packaging article.

Other aspects, features and embodiments of the invention will be more fully apparent from the ensuing disclosure and appended claims.

BRIEF DESCRIPTION OF THE DRAWINGS

FIGS. 3A-3E provide schematic representations of various steps of forming a packaging article as disclosed herein.

DETAILED DESCRIPTION OF THE INVENTION, AND PREFERRED EMBODIMENTS THEREOF

Figure 1:
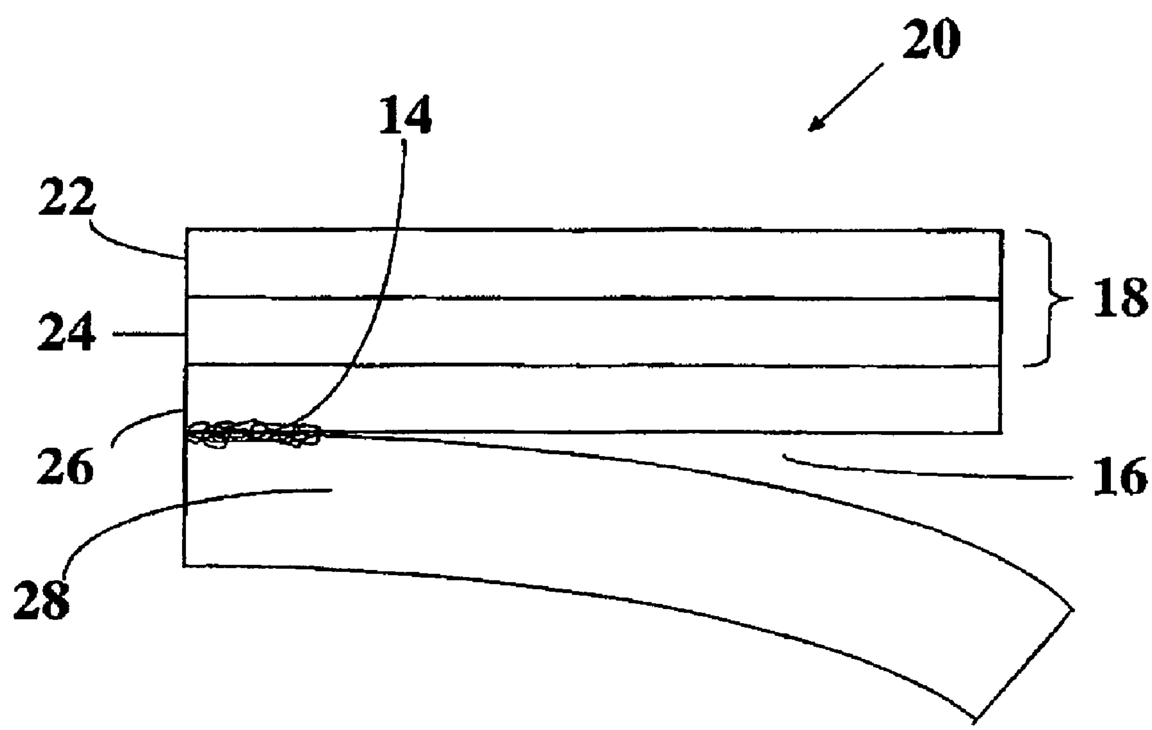
FIG. 1 is a schematic representation of a portion of a package according to one embodiment of the invention, showing the constituent laminae thereof.

The present invention is based on the discovery of a multilaminate construction that is usefully employed in the fabrication of containment structures to accommodate integrity testing and which concurrently allows the package to be formed with a porous sheet that is porous to sterilant gases such as steam or ETO in the sterilization of the package after its fabrication.

More specifically, the invention relates to a composite web article including porous sheet useful for forming packaging that is subjected to sterilant gases after the package is formed, in which the porous sheet has sealed to it an overlying sheet including a peelable polymeric film. The overlying sheet provides a non-porous barrier over the porous sheet. The overlying sheet can be a single layer sheet or it can be of multilayer character, formed for example by coextrusion and including a peelable layer and a non-porous backing layer. If of a single layer sheet construction, the overlying sheet is also non-porous. Regardless of its particular composition, the overlying sheet must be peelable from the porous sheet and must be non-porous in character.

By such construction, the overlying sheet including the peelable polymeric film permits compressed gas fill of the package for integrity testing, and after such testing is completed, the overlying sheet can be readily peelably removed from the underlying porous sheet, to yield the product package having a porous sheet as a structural member thereof. In this manner, the peel-away removal of the overlying sheet "exposes" the underlying porous sheet and facilitates penetration through the porous sheet, e.g., into the interior volume of the package, of sterilant gas such as steam and/or ETO.

In one embodiment, the invention provides a sterilizable bag constructed of a first sheet of a non-porous polymeric film, e.g., polyethylene film, and a facing sheet of a porous material, e.g., a paper (cellulosic web) or synthetic polymeric material, such as Tyvek® polyethylene sheet, with a peelable overlying sheet sealed to an exterior face of the facing sheet of porous material. For example the porous material and non-porous material sheets can be generally coextensive in area and in register with one another, being joined to one another by perimeter seams such as can be formed by thermal bonding, ultrasonic welding, adhesive bonding, or any other suitable technique. The porous sheet can alternatively be a fibrous web of a form analogous to Tyvek® film, but constituted of other synthetic resin polymeric material, e.g., polysulfone, polyimide, polypropylene, polybutylene, polyvinylchloride, polyurethane, polystyrene, etc.

The peelable overlying sheet can be a coextruded sheet including a peel-to-porous sheet layer (that is sealed to the exterior face of the facing sheet of porous material) and a non-porous polymeric layer such as a polyethylene backing layer on the peelable layer. The peelable layer can be formed of any suitable resin material, e.g., of a type that is used in peelable to Tyvek® films used in medical packaging where the peel property is used for opening the pouch or other container.

In this respect, it is to be noted that standard Tyvek® peel pouches the peelable layer thickness and seal temperatures are selected to obtain an opaque seal with a limited seal strength that is typically on the order of 5 Newtons/15 millimeters seal width. In the case of isolator bags or other Tyvek® bags that need integrity testing, the seal strength needs to be substantially higher, e.g., on the order of at least 20-25 Newtons/15 millimeters seal width. Such higher seal strength in turn requires a transparent seal that necessitates higher temperature for sealing. Since the making of the transparent seal requires higher temperatures, the construction of the peelable film must be modified in order to avoid damage to the peel layer. The present invention therefore embodies a substantial departure from the methods of the prior art that have been employed to form standard Tyvek® peel pouches, further evidencing the inventive character of the containment structures and package articles of the present invention.

In the foregoing illustrative embodiment involving a polyethylene film as a non-porous sheet member of the product package, the polyethylene can be of any suitable type, as suitable for steam- and/or ETO-sterilization. In the case of steam sterilization of the product package, the polyethylene is desirably a high density polyethylene (HDPE) material. In the case of sterilization by ETO, the polyethylene can be low density polyethylene (LDPE), linear low density polyethylene (LLDPE), or any other polyethylene. The porous layer of the final product package desirably is a Tyvek® sheet, and the peelable sheet overlying the Tyvek® sheet desirably is a peelable polyethylene sheet.

In this embodiment, the PE film/Tyvek® film/peelable PE film layers are sealed onto one another in forming the final product package, as a 3-layer bag. The pressurization integrity testing can be accommodated by providing a pressurization gas inlet, such as a spout, gland, or other inlet connector element, attached to the PE film in such manner as to allow ingress of gas therethrough into the interior volume of the container package. The integrity test then is simply carried out by testing the bag for pressure loss when the bag is filled with compressed air. The integrity test can be performed after production (sealing) of the bag or after the filling of the bag with the product article, as necessary or desirable in a given end use application of the invention. After a (successful) integrity test, peelable PE film can be readily peeled off manually, or automatically (e.g., by a suction plate element joined by suitable conduit to a vacuum pump), and the bag can be submitted to steam- and/or EPO-sterilization.

In the foregoing illustrative embodiment employing PE film/Tyvek® film/peelable PE film layers, the sealing parameters are desirably set to seal all three layers against each other resulting in a strong PE/Tyvek® film seal having a seal strength greater than about 20 Newtons/15 millimeters seal width, and a peelable Tyvek® film/peelable PE seal on the order of about 5 Newtons/15 millimeters seal width, e.g., in a range of from about 1 to about 8 Newtons/15 millimeters seal width.

The component layers of multilayer films and packaging sheet thicknesses in the broad practice of the present invention can be readily determined without undue experimentation within the skill of the art, based on the disclosure herein, to provide packaging with appropriate properties for the specific contained product and ultimate use and storage environments of the packaging. In general, the Tyvek® sheets used in the practice of the invention, or alternatively of other porous material sheets, should have a thickness that provides appropriate structural strength and integrity to the packaging, e.g., in a thickness range of from about 25 micrometers to about 3 millimeters, and the peelable layers and non-porous sheets employed in the practice of the invention can for example be of thickness in a corresponding range of thickness values.

It will be recognized that while the invention is illustratively described herein with reference to packaging that includes porous and non-porous sheet materials, the invention is also susceptible of implementation in packaging in which the entire package as ultimately used is formed of a sheet or web material that is porous in character. In such totally porous packaging, the respective walls or sheet portions of the package can be overlaid with peelable films conferring temporary non-porous character to the packaging and allowing the integrity testing of the package or portions thereof. The invention thus has broad applicability, and the illustrative embodiments herein described, having porous and non-porous sheets as structural elements thereof, relate to one form of the invention.

FIG. 1 is a schematic representation of a portion of a package 20 according to one embodiment of the invention, showing the constituent laminae thereof.

The package 20 comprises a porous material layer 26, such as Tyvek® sheet, which is bonded to non-porous sheet 28, e.g., of polyethylene, by fusion bond 14 as shown. The fusion bond 14 can be formed by ultrasonic welding of the sheets 26 and 28 to another at their registered edges, using a Branson ultrasonic welder (Branson Products, Inc., Danbury, Conn.) or other suitable ultrasonic welding tool. The bonded sheets 26 and 28, joined at their edges, thereby define an enclosed interior volume 16 therebetween, for containment of a product article therein, e.g., a medical device or therapeutic agent.

On the exterior face of the porous material layer 26 (the top surface in the view shown), is sealed the peelably removable sheet 18. In the illustrated embodiment, the peelable sheet 18 is of a 2-layer construction, including a first layer 24 of a peelable polymeric film material in facial contact with the porous material sheet 26, and a second layer 22 of a backing material, e.g., polyethylene. The overlying sheet 18 remains in sealing contact with the porous sheet 26 during the pressurization testing of the integrity of the package, and thereafter overlying sheet 18 is peeled away and removed from the porous sheet 26.

Figure 2:
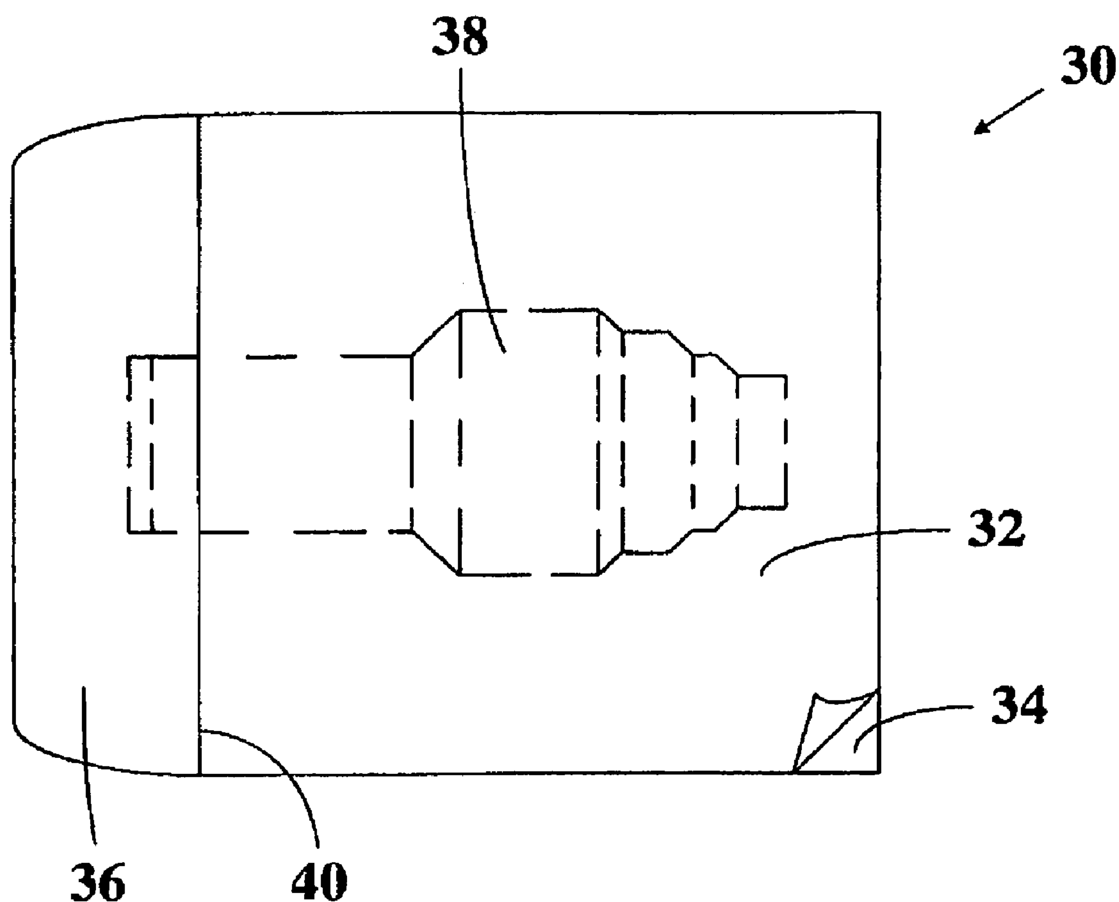
FIG. 2 is a top plan view of a package according to another embodiment of the invention, containing a catheter coupling assembly, as employed for interconnecting a catheter to an angiographic syringe.

FIG. 2 is a top plan view of a package 30 according to another embodiment of the invention, containing a catheter coupling assembly 38, as employed for interconnecting a catheter to an angiographic syringe.

The package 30 comprises a non-porous package member 36 which can be of a tray or cassette form, defining a receptacle within which the catheter coupling assembly is disposed. The non-porous package member 36 has a cover bonded thereto, e.g., along the seam line 40. The cover member comprises a porous material sheet 34 as an underlying element thereof, and an overlying sheet 32, which as shown in the lower right-hand portion of the product package is partially peeled away from the underlying porous material sheet 34. The overlying sheet can be a coextruded sheet formed of a peel layer and a backing layer, as described hereinabove, or the overlying sheet can be a single-layer sheet of a peelable and non-porous material.

FIGS. 3A-3E show various steps of fabricating a packaging article 20. FIG. 3A shows a first porous layer 26 being applied to a nonporous layer 28, optionally including a spout or gland 15. FIG. 3B shows formation of fusion bonds 14 along three peripheral edges between the porous sheet 26 and the underlying nonporous sheet 28. FIG. 3C shows application of a peelable layer 18 to the porous sheet 26. FIGS. 3D-3E show two views of the packaging article 10 having an open end.

Figure 4A:
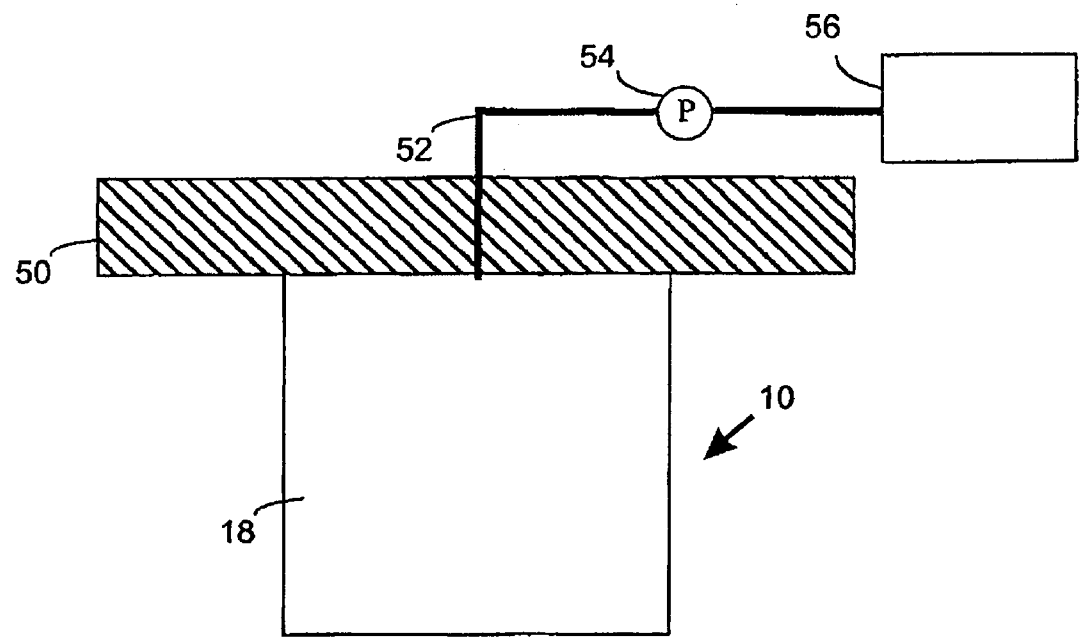
FIG. 4A shows a packaging article subject to pressurization testing in a clamping apparatus.
Figure 4B:
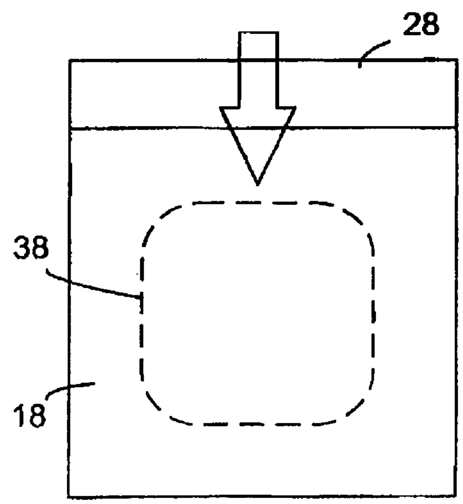
FIG. 4B shows a step of inserting a product article into a packaging article according to the invention.

FIG. 4A shows a packaging article 10, having a peelable nonporous sheet 18 intact, subject to pressurization testing in a clamping apparatus 50 having a gas conduit 52, pressure gauge 54, and pressurization gas source 56. Such clamping apparatus 50 establishes a temporary seal along one end of the packaging article 10 sufficient to enable pressurized gas to be retained upon admission (either through conduit 50 or a spout 15 shown in FIG. 3A) thereto. Upon release of such clamping apparatus, a product article 38 device may be inserted into the interior of the packaging article 10 via an open end thereof, as shown in FIG. 4B. Such packaging article may then be sealed by fusion bond 14, as shown in FIG. 4C.

Figure 4C:
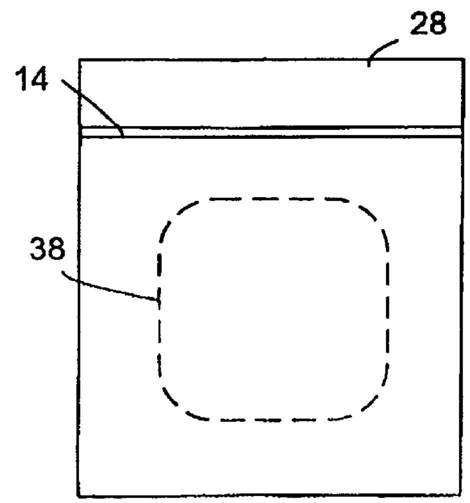
FIG. 4C shows sealing of the product article into the packaging article of FIG. 4B.
Figure 4D:
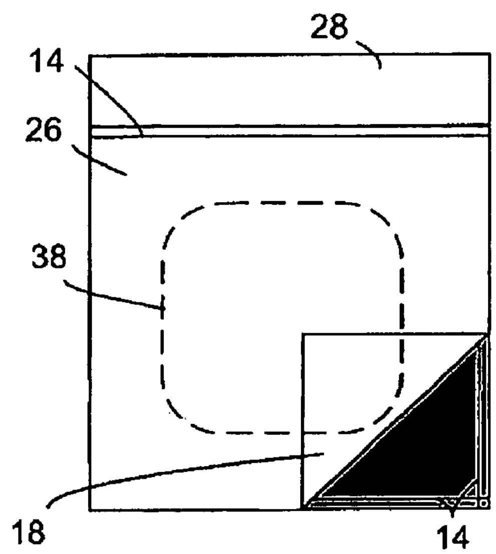
FIG. 4D shows peelable removal of a nonporous cover layer from a porous sheet of a packaging article containing a product article, according to the invention.
Figure 4E:
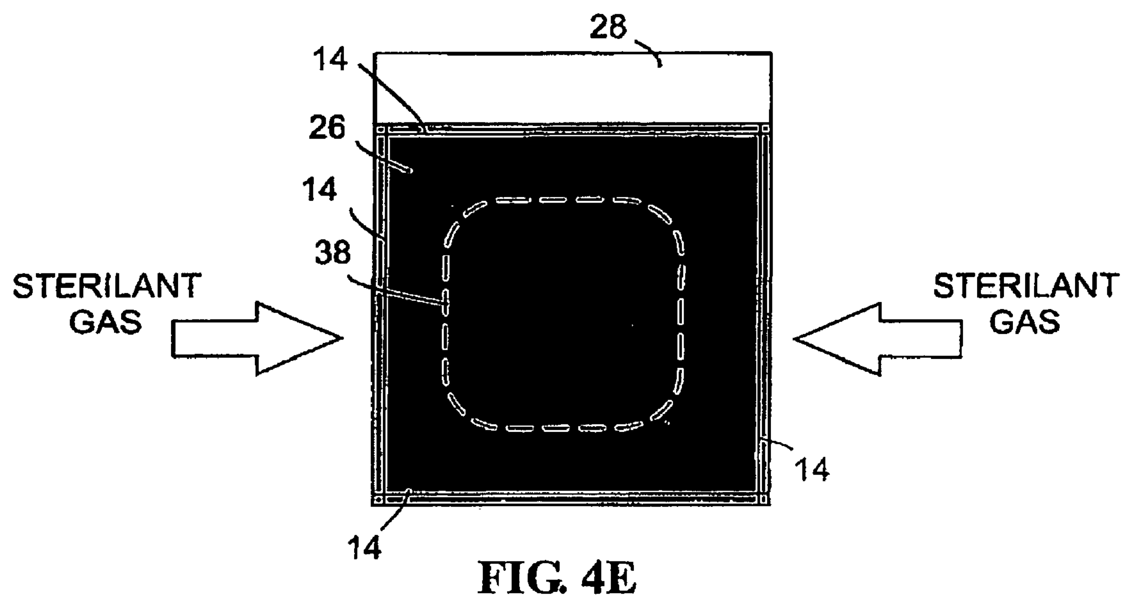
FIG. 4E shows application of a sterilant gas to a packaging article having an exposed porous material and containing a product article therein.

FIG. 4D shows a product article 38 disposed within the sealed packaging article of FIG. 4C, with the peelable cover 18 being in the state of removal by peeling from the lower right corner thereof to expose the porous material 26. FIG. 4E shows application of sterilant gas through the porous material 26, following removal of nonporous layer 18, to sterilize the product article 38 within the packaging article.

It will therefore be seen that the present invention provides a composite film structure that is usefully employed for forming packaging that must be subjected to pressurization integrity testing, and which in subsequent processing must be sufficiently pervious to sterilant gases.

The specific film and sheet materials used in the packaging of the invention can be widely varied in the practice of the invention, as is readily determinable within the skill of the art, based on the disclosure herein. In like manner, the thicknesses of the specific film and sheet materials are widely variable, depending on the integrity test pressure conditions and the ultimate requirements of the product that is contained in the package.

It will therefore be recognized that while the invention has been described herein in reference to specific aspects, features and illustrative embodiments of the invention, it will be appreciated that the utility of the invention is not thus limited, but rather extends to and encompasses numerous other aspects, features and embodiments. Accordingly, the claims hereafter set forth are intended to be correspondingly broadly construed, as including all such aspects, features and embodiments, within their spirit and scope.

What is claimed is:

1. A method of integrity testing a packaging article by pressure retention testing and rendering said packaging article permeable to sterilant gas for sterile packaging of a product article therein after said pressure retention testing, and sterilizing the packaging, said method comprising:

(a) providing said packaging article comprising at least one peripherally bonded sheet, including a first sheet of a porous material that is permeable to passage of sterilant gas therethrough in exposure to a sterilant gas environment, wherein a peelable film that is non-porous to passage of said sterilant gas therethrough is in facial contact with the first sheet of porous material, said peelable film being peelably removable from the first sheet;

(b) pressurizing said packaging article by a compressed gas and monitoring pressure retention by the packaging article to determine its integrity;

(c) after completion of step (b) with a verification of said integrity, removing the peelable film from the first sheet to expose the first sheet for passage of said sterilant gas therethrough; and (d) after step (c), exposing said packaging article to said sterilant gas to sterilize said packaging article.

2. The method of claim 1, further comprising the step of inserting a product article within said packaging article, wherein step (d) is carried out after said inserting step.

3. The method of claim 1, wherein said sterilant gas comprises steam and/or ETO.

4. The method of claim 1, wherein said sterilant gas comprises steam.

5. The method of claim 1, wherein said sterilant gas comprises ETO.

6. The method of claim 1, wherein said first sheet comprises a cellulosic material.

7. The method of claim 6, wherein said cellulosic material comprises paper.

8. The method of claim 1, wherein said first sheet comprises a synthetic polymeric material.

9. The method of claim 8, wherein said synthetic polymeric material comprises polyethylene.

10. The method of claim 9, wherein the polyethylene comprises high-density polyethylene.

11. The method of claim 1, wherein said first sheet comprises a flash-spun and bonded polymeric fibrous web.

12. The method of claim 11, wherein said web comprises high-density polyethylene fiber.

13. The method of claim 1, wherein said first sheet comprises a porous web of a material selected from the group consisting of polyethylene, polysulfone, polyimide, polypropylene, polybutylene, polyvinylchloride, polyurethane, and polystyrene.

14. The method of claim 1, wherein said first sheet comprises a film of heat- and pressure-consolidated flash-spun high density polyethylene fibers.

15. The method of claim 1, wherein the peelable film comprises a synthetic resin polymeric film.

16. The method of claim 15, wherein the synthetic resin polymeric film comprises polyethylene film.

17. The method of claim 1, wherein the peelable film comprises a backing layer.

18. The method of claim 17, wherein the backing layer comprises a synthetic resin material.

19. The method of claim 18, wherein the backing layer synthetic resin material comprises polyethylene.

20. The method of claim 1, wherein the packaging article further comprises a non-porous structural component, peripherally bonded to said first sheet to form therewith an enclosure for containment of said product article.

21. The method of claim 20, wherein said non-porous structural component comprises a non-porous second sheet.

22. The method of claim 20, wherein said non-porous structural component comprises a shaped member peripherally bonded to said first sheet and forming therewith an enclosed interior volume for containment of said product article therein.

23. The method of claim 1, wherein the packaging article comprises a bag adapted to hold said product article therein.

24. The method of claim 23, wherein said bag comprises a non-porous polyethylene sheet peripherally bonded to said first sheet.

25. The method of claim 24, wherein said first sheet comprises a film of heat- and pressure-consolidated flash-spun high density polyethylene fibers, and said peelable film comprises a polyethylene film.

26. The method of claim 1, wherein said product article comprises a medical device.

27. The method of claim 1, wherein the product article comprises a pharmaceutical agent.

28. The method of claim 1, wherein the packaging article comprises a bag including said first sheet as a panel of the bag, wherein the first sheet is peripherally bonded along an edge region of said first sheet to a non-porous panel to form therewith an enclosed interior volume for holding said product article, wherein said first sheet comprises a film of heat- and pressure-consolidated flash-spun high density polyethylene fibers, said peelable film comprises a peelable polyethylene film, and said non-porous panel is formed of polyethylene film.

29. The method of claim 28, wherein the bonded edge region has a bond strength greater than 20 Newtons per 15 millimeter bonded edge region width.

30. The method of claim 29, wherein the peelable film is sealed to the first sheet with a seal strength in a range of from 1 to 8 Newtons per 15 millimeters seal width.

31. The method of claim 1, wherein the packaging article comprises a pressurization gas inlet.

32. The method of claim 31, wherein the pressurization gas inlet comprises a spout.

33. The method of claim 31, wherein the pressurization gas inlet comprises a gland.

34. The method of claim 31, wherein the pressurization gas inlet comprises an inlet connector element.

35. The method of claim 1, wherein said at least one sheet includes the first sheet and a second sheet, wherein the first sheet and the second sheet are peripherally bonded along multiple edges thereof.

* * * * *